United States Patent
Busam et al.

(10) Patent No.: US 7,427,434 B2
(45) Date of Patent: Sep. 23, 2008

(54) SELF-BONDED CORRUGATED FIBROUS WEB

(75) Inventors: Ludwig Busam, Huenstetten (DE); Martin Geoffrey Scaife, Köln (DE); Matthias Rudolf Sprehe, Kerpen-Sindorf (DE); Gabriele Stiehl, Schwalbach a. Ts. (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/689,342

(22) Filed: Oct. 20, 2003

(65) Prior Publication Data

US 2005/0100713 A1 May 12, 2005

Related U.S. Application Data

(63) Continuation of application No. PCT/US02/12454, filed on Apr. 19, 2002.

(30) Foreign Application Priority Data

Apr. 20, 2001 (EP) .................................... 0109745

(51) Int. Cl.
 B32B 3/28 (2006.01)
(52) U.S. Cl. ....................... 428/182; 428/183
(58) Field of Classification Search ................ 428/181, 428/182, 183, 173
See application file for complete search history.

(56) References Cited

U.S. PATENT DOCUMENTS

| 1,975,548 | A | * | 10/1934 | Ives .......................... 428/167 |
| 2,494,723 | A | | 1/1950 | Rowe |
| 3,653,382 | A | * | 4/1972 | Easley et al. ................. 604/370 |
| 3,839,137 | A | * | 10/1974 | Davis et al. .................. 428/183 |
| 4,267,223 | A | * | 5/1981 | Swartz ....................... 428/172 |
| 4,806,300 | A | | 2/1989 | Walton et al. |
| 5,906,879 | A | | 5/1999 | Huntoon et al. |
| 6,171,682 | B1 | * | 1/2001 | Raidel et al. ................. 428/182 |
| 6,506,472 | B1 | * | 1/2003 | Tanaka et al. ............... 428/105 |
| 6,548,147 | B1 | | 4/2003 | Raidel et al. |
| 6,586,076 | B1 | * | 7/2003 | Mizutani et al. ............ 428/173 |

FOREIGN PATENT DOCUMENTS

| EP | 0 124 637 A1 | 11/1984 |
| EP | 1 090 615 A1 | 4/2001 |
| EP | 1 103 240 A1 | 5/2001 |
| JP | 56-140153 | 11/1981 |
| JP | 1998506333 A | 6/1998 |
| JP | 2001137284 A | 5/2001 |

* cited by examiner

*Primary Examiner*—Donald Loney
(74) *Attorney, Agent, or Firm*—Jay A. Krebs; Thibault Fayette; Matthew P. Fitzpatrick

(57) ABSTRACT

A self-bonded corrugated web made from a primary pre-bonded web layer of thermoplastic fibers having a substantially uniform thickness. The primary pre-bonded web layer is arranged to form corrugations forming a corrugation pattern of parallel corrugation lines, which can be parallel to the longitudinal extension of the web. The corrugated web is heat- or melt-fusion bonded in regions forming a primary bonding pattern of a plurality of primary bonding pattern lines, which are arranged non-parallel to the corrugation lines and which intersect at least two of the corrugation lines, for stabilizing the corrugations.

12 Claims, 10 Drawing Sheets

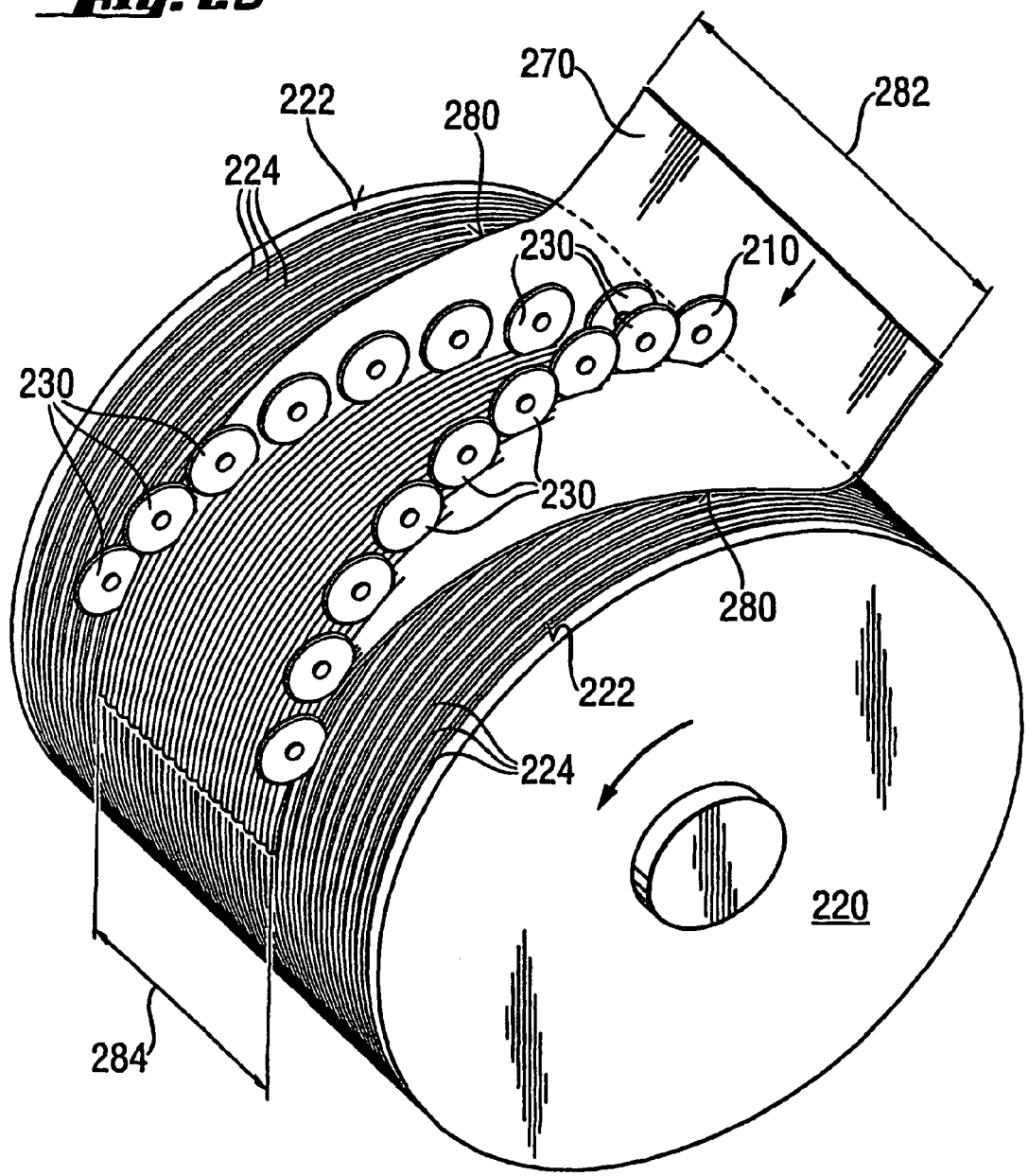

SELF-BONDED CORRUGATED FIBROUS WEB

CROSS REFERENCE TO RELATED APPLICATION

This application is a continuation of International Application PCT/US02/12454, with an international filing date of Apr. 19, 2002, claiming priority to EP Application No. 01/09745.8 filed Apr. 20, 2001.

FIELD OF THE INVENTION

The present invention relates to a self-boded corrugated fiber containing web, a process and an apparatus for producing such a web and an article comprising such a web, in particular a disposable hygiene article such as a baby or adult incontinence diaper, a feminine care product, a wipe, or the like.

BACKGROUND

Corrugated web materials are well known in the art to be used in various applications as a material as such or as a component in the manufacturing of articles. In order to arrive at such webs, essentially flat raw materials are supplied to a process which three-dimensionally shapes such corrugations. Corrugated web material yield a wide variety of benefits including low-density for a desired stability, but also can provide good softness. Typical corrugation materials include sheets, films, foams, and the like, as well as woven or non-woven materials.

When corrugated materials are used in the manufacture of articles, the corrugated shape can be created during this manufacturing process ("on-line") or separately, such as "off-line" shaping with subsequent shipment or transport to this manufacturing site. Due to the voluminous configuration, the "on-line" process is often preferred.

There exist in the art processes for forming corrugation of materials such as for example U.S. Pat. No. 4,806,300 (Walton et al.). During such processes, the materials are corrugated by being fed through two interpenetrating corrugated rolls. This procedure, however, leads to stretching of the material and potentially to plastic deformation in the transverse direction. In turn, such stretching and plastic deformation may change the physical structure of the material and hence its properties.

U.S. Pat. No. 5,906,879 describes a ultra-resilient three-dimensional non-woven fiber material, wherein the shape is maintained by means of a heat-activatable adhesive component incorporated into the structure. WO 96/00625 (Raidel et al) describes the forming of corrugations by means of a guide bed, and co-pending EP-application 99 12 46 37 (Dziezok et al., filed Dec. 19, 1999, case attorney docket number CM02251FQ) discloses a process for forming longitudinal corrugations in a web material by means of intermeshing groove rolls. In both cases, the corrugations are formed in longitudinal direction of the web while the web is not restricted in transverse direction, such that the overall width of the web is reduced. After the corrugations are formed, they are stabilized by an added component, such as adhesive stabilization within the web as in the above mentioned US'879, by attaching a flat support web to the corrugations, or by plastically deforming the web along the lines of corrugation.

SUMMARY OF THE INVENTION

The present invention is a self-bonded corrugated web made from a primary pre-bonded web layer of substantially uniform thickness, which contains thermoplastic fibers, and which is arranged to form corrugations forming a corrugation pattern of parallel corrugation lines, which can be parallel to the longitudinal extension of the web, whereby the corrugated web is heat- or melt-fusion bonded in regions forming a primary bonding pattern of a plurality of primary bonding pattern lines, which are arranged non-parallel to the corrugation lines and which intersect at least two of the corrugation lines, thereby stabilizing the corrugations. Preferably, each of the corrugation lines is connected to at least one neighboring corrugation line by at least one primary bonding pattern line.

The primary bonding pattern can comprise first and second primary bonding pattern lines, whereby the first primary bonding pattern lines can be essentially parallel to each other, and the second primary bonding pattern lines can be parallel to each other, and the first and the second primary pattern lines are in a non-parallel arrangement to each other. The first and second primary bonding pattern lines can be intersecting lines, circumscribing regions, which are unbonded by the primary bonding pattern. These regions contain at least 3, preferably at least 5, and more preferably at least 9 corrugations, and can contain less than 20, preferably less than 15 corrugations.

The primary bonding pattern lines can be continuous lines, preferably straight lines, and the primary bonding pattern can consist of a secondary bonding pattern consisting of a plurality of bonding points.

A corrugated web according to the present invention preferably exhibits a low pressure loft of at least 18 $[\mu m/(g/m^2)]$ preferably of more than 21 $[\mu m/(g/m^2)]$ and even more preferably of more than about 23 $[\mu m/(g/m^2)]$, and a high pressure loft of at least 11 $[\mu m/(g/m^2)]$, preferably more than about 13 $[\mu m/(g/m^2)]$, and even more preferably of more than about 18 $[\mu m/(g/m^2)]$.

The present invention further relates to an absorbent article having an absorbent core, a backsheet towards the garment oriented side of the core, and a self-bonded web positioned on the wearer oriented side of the core.

The present invention relates even further to a method of shaping and bonding a primary web for forming a self-bonded corrugated web, which comprises the steps of first, providing an essentially flat fiber containing pre-bonded primary web, second, shaping the web into corrugations to form corrugation lines,and thirdly autogenously bonding fibers of the corrugated web by means of a primary bonding pattern of a plurality of primary bonding pattern lines, which are arranged non-parallel to the corrugation lines and intersecting at least two of these corrugation lines The corrugations can form vale and crest regions and the bonding of the fibers of the web can be essentially only applied to the vale regions. The method can also comprise the step of deforming the formed corrugations prior to bonding in the region of the primary bonding pattern so as to form overlaying layers of the primary web, which are bonded to each other in the subsequent bonding step.

BRIEF DESCRIPTION OF THE FIGURES

FIG. 2B shows a perspective view of a section of this apparatus.

DETAILED DESCRIPTION OF THE INVENTION

Figure 1:
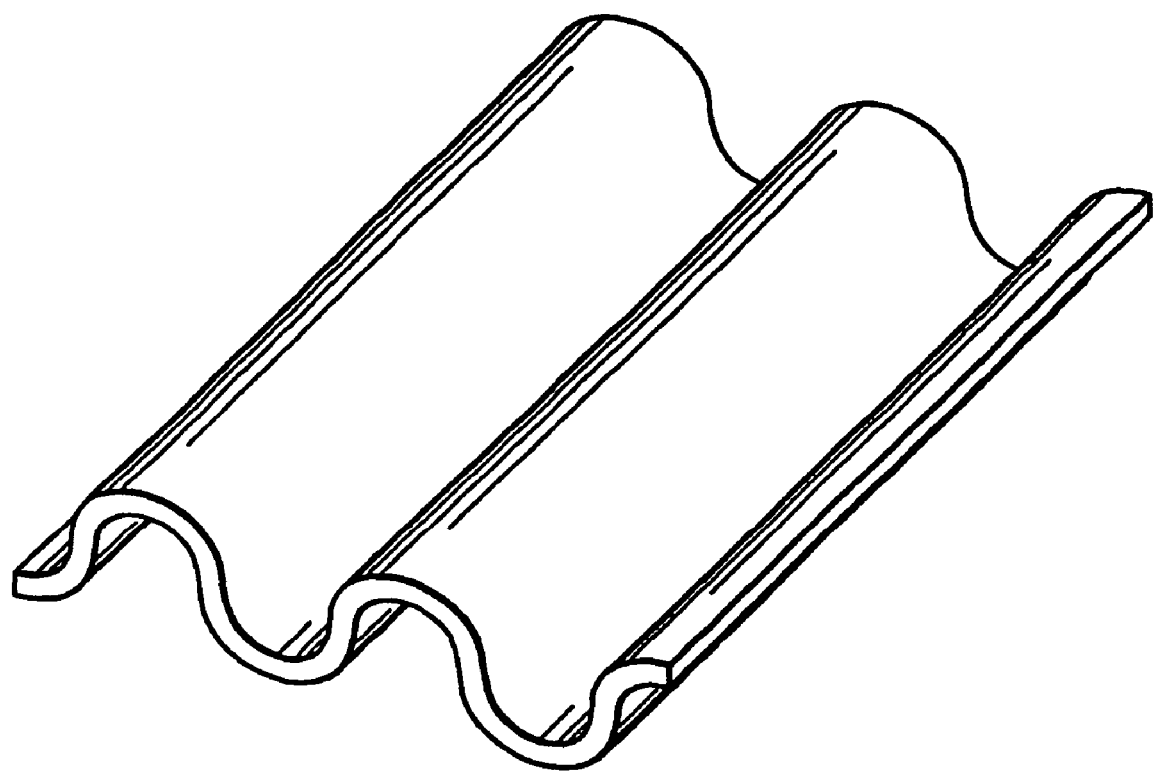
FIG. 1 is a schematic presentation of corrugations.

Web materials useful for the present invention are sheet like materials, consisting of or comprising a fibrous sheet. The web material has a longitudinal dimension, a transverse dimension, and a thickness dimension. The longitudinal dimension of the material is substantially larger than the transverse dimension and both are substantially larger than the thickness dimension. Typically, the material is supplied to the manufacturing process along the longitudinal dimension. Accordingly, the material is ideally rendered virtually infinite in the longitudinal dimension by splicing together a plurality of stretches of web material. By cutting the web material perpendicular to the longitudinal dimension, pieces of the material suitable for incorporation into an article of manufacture are obtained. Due to the sheet like nature of the web material, the thickness dimension is typically smaller than the thickness dimension of the corrugated material. Such web materials are useful for the production of articles, in particular disposable articles including disposable absorbent articles such as diapers, sanitary napkins, adult incontinence products, and the like.

Webs suitable for being used in the present invention are preferably "essentially flat", which refers to webs, which have a length and width dimension significantly exceeding their z- or thickness dimension, and wherein the thickness is essentially the same throughout the length and width dimension. The densities of the primary webs can vary over a wide range, and can be less than about 0.1 g/cm$^3$, less than about 0.05 g/cm$^3$, or even less than 0.03 g/cm$^3$, or can be more than 0.15 g/cm$^3$, or even more than 0.2 g/cm$^3$. Suitable webs can have a wide range of basis weights, and can have basis weights as low as 15 g/m$^2$. Typically, basis weights will be higher than about 20 g/m$^2$, or even higher than 40 g/m$^2$, but can be more than 80 g/m$^2$, more than 100 g/m$^2$ or even more than 200 g/m$^2$.

The web materials suitable for the present invention comprise fibrous materials to form fibrous web or fibrous matrices. Fibers useful in the present invention include those that are naturally occurring fibers (modified or unmodified), as well as synthetically made fibers. Examples of suitable unmodified/modified naturally occurring fibers include cotton, Esparto grass, bagasse, kemp, flax, silk, wool, wood pulp, chemically modified wood pulp, jute, rayon, ethyl cellulose, and cellulose acetate.

Suitable synthetic or thermoplastic fibers can be made from any thermoplastic polymer that can be melted at temperatures that will not extensively damage the composition. Preferably, the melting point of this thermoplastic material will be less than about 190° C., and preferably between about 75° C. and about 175° C. Preferably, the melting point of this thermoplastic material should be no lower than the temperature at which the thermally bonded structures are likely to be stored or used in articles such as in disposable absorbent articles. The melting point of the thermoplastic material is typically no lower than about 50° C. Thus, such fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used in the present invention can be of one type, or of different types, and if different fibers are used, these can be homogeneously mixed, randomly distributed, or arranged in a predetermined distribution. Webs suitable for use in the present invention need to comprise a sufficient amount of self-, heat- or melt-bondable fibers, so as to allow bonding within the web structure.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. Then, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. bent). Bicomponent fibers can be crimped by typical textile means such as, for example, a stuffer boy method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable thermoplastic fibers can have a decitex in the range from about 1.0 to about 20, preferably from about 1.4 to about 10.

For many uses according to the present invention, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 gram per square of centimeter of thermoplastic fiber.

Suitable wood pulp fibers for being added to the web can be obtained from well-known chemical processes such as the Kraft and sulfite processes, but also ground wood, refiner mechanical, thermomechanical, chemomechanical, and chemothermomechanical pulp processes can be used to provide wood pulp fibers, or recycled or secondary wood pulp fibers, as well as bleached and unbleached wood pulp fibers, can be used. A desirable source of hydrophilic fibers for use in the present invention is chemically stiffened cellulosic fibers, such as described in more detail in disclosed in U.S. Pat. No. 3,224,926 (Bernardin), issued Dec. 21, 1965; U.S. Pat. No. 3,440,135 (Chung), issued Apr. 22, 1969; U.S. Pat. No. 3,932, 209 (Chatterjee), issued Jan. 13, 1976; and U.S. Pat. No. 4,035,147 (Sangenis et al), issued Dec. 19, 1989; U.S. Pat. No. 4,898,642 (Moore et al), issued Feb. 6, 1990; and U.S. Pat. No. 5,137,537 (Herron et al), issued Aug. 11, 1992.

The fibers as described in the above are formed into an uncorrugated ("primary") sheet, such by a variety of processes known as such in the art. When considering the individualized fibers as a starting material for making a web, these can be laid down in a fluid medium—if this is gaseous (air) such structures are generally referred to as "dry-laid", if it is liquid such structures are generally referred to as "wet-laid". "Wet-laying" is broadly used to produce paper tissues with a wide range of properties. This term is most commonly used with cellulosic materials, however, also synthetic fibers can be included. Alternatively, the carding process can be used to form such webs.

Further, a molten polymer can be extruded into fibers which then can be formed directly into a web (i.e. omitting the process step of making individual fibers which then are formed into a web in a separate process step). The resulting structures are commonly referred to as non-wovens of the meltblown type or—if fibers are significantly more drawn—spunbonded webs. Further, webs can also be formed by combining one or more of the other formation technologies.

In order to give sufficient strength and integrity properties to the webs to allow further handling according to the present invention, these are generally pre-bonded (i.e. bonded before they are submitted to the process step according to the present invention to form structures and products according to the present invention). The most broadly used technologies are (a) chemical bonding or (b) thermo bonding by melting a part of the web such.

For the latter, the fibers can be compressed, resulting in distinct (pre-) bonding pattern such as of bonding points known as such well in the art, which, for example for non-woven materials, can cover a significant portion of the total area, and values of 20% are not uncommon. Or—particularly useful for structures where low densities are desired—"airthrough" bonding can be applied, where parts of the polymers (e.g. the sheath material of a BiCo-fibers) are molten by means of heated air passing through the (often air-laid) web.

The web can also pre-bonded by means of a chemical additive or binding means to consolidate the fibers into a web without melt-bonding the fiber polymers. Such chemical additive binding means for increasing physical integrity of the absorbent member can be resinous binders, latex, styrene-butadiene-rubber (SBR), Ethylene-vinyl-acetate (EVA), Ethylene-vinyl-alcohols (EVOH), Acrylic based resins, and starch known in the art for providing increased integrity to fibrous webs. Preferred chemical binders are of the Styrene-Butadiene type, such as supplied by GenCorp, Mogadore, Ohio, USA, or by BASF AG, Ludwigshafen, FRG. In a particular execution, the resin for pre-bonding the web has a high glass transition temperature $T_g$ (as can be determined by conventional analytical tools such as Differential Scanning Calorimetry—DSC), such as a $T_g$ of more than 0° C., even more preferred more than 15° C. However, $T_g$ should not be higher than the softening temperature of the fiber resin.

The chemical binder means can be applied in various physical forms, such as particles. Preferably. it is applied in the liquid form which can be achieved in a number of conventional ways, generally such as running the web through a bath, or over wetted rolls, or spraying the binder onto the web. The chemical binding means can be applied homogeneously and evenly throughout the web, or in a non-uniform application. The total amount of added resin is not critical for the present invention, generally a weight percentage of resin in the final, dried and cured web (i.e. excluding a carrier for the resin, which has been dried off) of between 10% and 50% is suitable, a preferred range is between 20% and 35%, and a most preferred amount is between 25% and 10%. After the binder is applied to the web, it has to be cured and dried to create the prebonding. This refers to two effects, namely to provide a certain curing of the resin thus bonding both to itself but also to the fibers and also to remove water or other carrier fluid for the resin.

The pre-bonding of the web can be achieved by a number of conventional techniques, generally aiming at providing energy to the web, such as running the web over heated rolls, through a heated oven, or treating it with infra-red energy beams. For certain applications, it may be preferred that the web is not compressed in its thickness dimension (or z-direction) during this process.

In addition to forming and pre-bonding the primary web, this can be further treated to modify specific properties. This can be—as one of many possible examples—additional surfactant to render hydrophobic fibers more hydrophilic, or vice versa. For certain applications, it may be desirable to combine the fibrous web with another material, such as another fibrous web, or a coating, or a film. This other material should be compatible with the primary use of the material, such that, for example, a film material should be liquid permeable, if the corrugated web according to the present invention should be liquid permeable. The primary web material may also comprise non-fibrous material, such as particulate material, as long as at least a part of the primary web structure remains fibrous.

The term "corrugation" as used herein refers to geometrical structures, having vales and crests arranged in a repeating, generally parallel arrangement, such that the corrugated structure has a thickness dimension substantially larger than the thickness dimension of the non-corrugated primary web material or of a non-corrugated portion of the material. The corrugation may have a wide variety of cross-sectional shapes including but not being limited to rectangles, triangles, sinusoidal curves, circular segments hyperbolic, parabolic, triangular square, and the like. A typical shape for corrugations is depicted in FIG. 1. The corrugations do not need to be constant over the total web, such that a web can have corrugations having a varying depth, or distances.

The corrugated web according to the present invention preferably has a thickness dimension of at least 150 percent of the thickness dimension of the primary web material, more preferably of at least 200 percent, even more preferably of at least 300 percent and most preferably has a thickness dimension of at least 500 percent of the thickness dimension of the primary web material.

The corrugations can be formed in straight lines, or in curvelinear lines, having a general orientation, as defined by the orientation of the vales and/or crests, which extends across the width of a web material (i.e. CD-orientation), or along the length of the material (i.e. MD-orientation), or can be at an angled positioning relative to the length or width direction.

The creation of corrugations is well known in principle. A preferred execution is described in detail in U.S. Pat. No. 2,494,723 (Rowe); U.S. Pat. No. 4,806,300 (Walton et al.); U.S. Pat. No. 5,906,879 (Huntoon), WO 96/00625 (Raidel et al), and co-pending EP-application 99 12 46 37 (filed Dec. 19, 1999, case attorney docket number CM02251FQ), all of which are incorporated herein by reference as far as the forming of a corrugations is concerned. EP-A-0.341.993 discloses also the formation of corrugations in a direction perpendicular to the (essentially endless) longitudinal direction of the material.

Figure 2A:
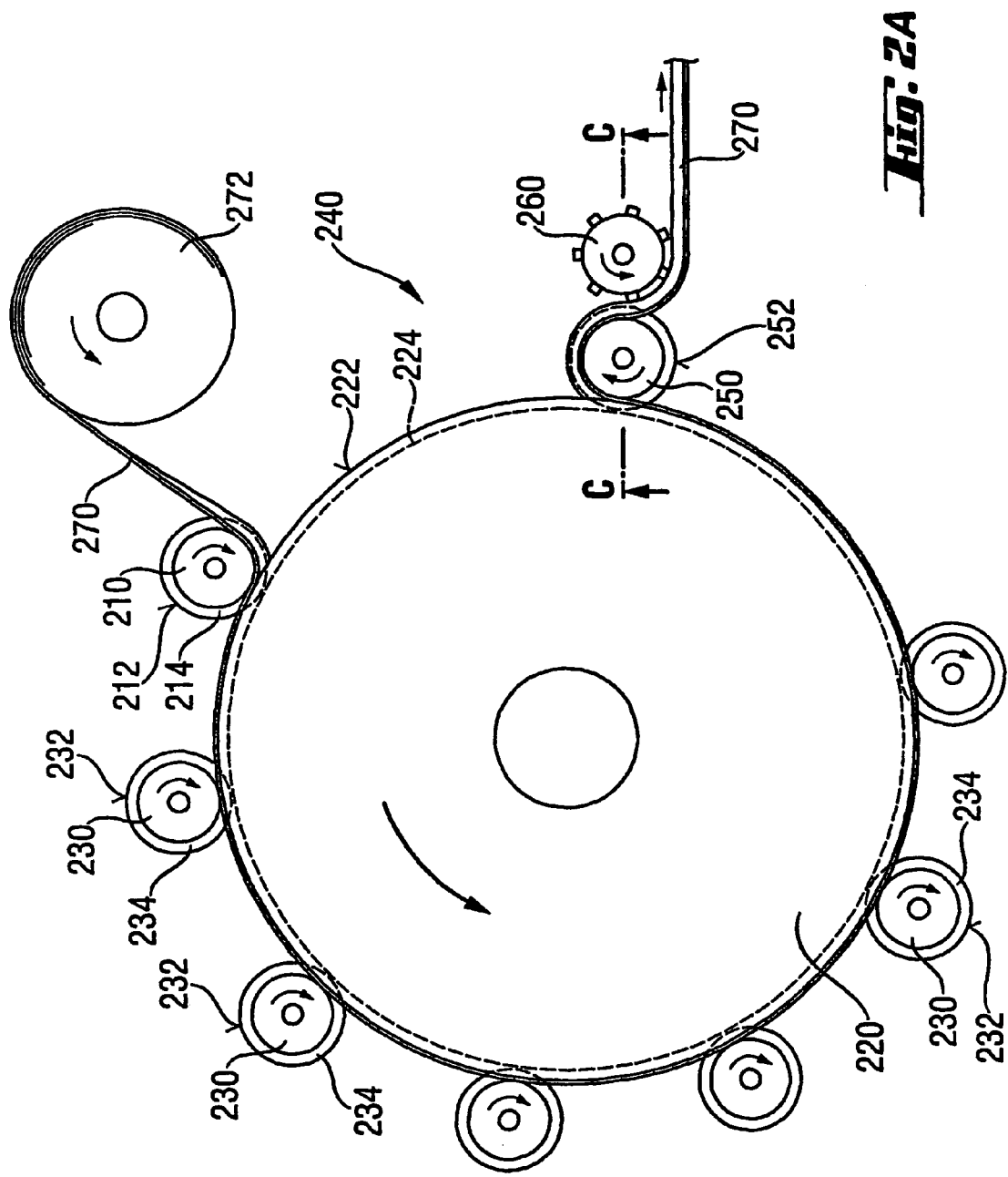
FIG. 2A is a schematic presentation of an apparatus of the present invention.

An apparatus suitable for the present invention is shown schematically in FIGS. 2A, B, C, D, and E, wherein for corresponding elements corresponding numeral have been used. The apparatus 240 comprises a drum 220 of generally cylindrical form being rotatable around its symmetry axis. The drum has an outer surface 222 and has a diameter which is twice the distance from the symmetry axis to the outer surface 222. The outer surface 222 has a longitudinal direction which is substantially parallel to the perimeter of the cylindrical drum and the outer surface 222 has a transverse direction which is substantially perpendicular to the longitudinal direction. The drum 220 further comprises on its outer surface 222 a plurality of longitudinal grooves 224. The depth of the longitudinal grooves 224 is directed radially inward from the outer surface 222. The apparatus 240 further comprises a first roll 210 of generally cylindrical form. First roll 210 is rotatable around its symmetry axis and comprises an outer surface 212 and a diameter defined in analogy to the drum 220. First roll 210 further comprises on it's outer surface a longitudinal protuberance 214 extending radially outward from the outer surface 212. The apparatus 240 further comprises a number of second rolls 230 of generally cylindrical form. The longitudinal protuberance 240 corresponds in geometry to at least one groove 224. Second rolls 230 are rotatable around their symmetry axis and comprise outer surfaces 232 and diameter defined in analogy to the drum 220. Second rolls 230 further comprise on the outer surface an increasing number of longitudinal protuberances 234 extending radially outward from the outer surface 232. The longitudinal protuberances 234 correspond in geometry to the grooves 224. Alternatively, as depicted in FIG. 2B, a number of second rolls 230 each having one protuberance only, can be arranged in staggered positions circumferentially to drum 220. First roll 210, and second rolls 230 are positioned in proximity to at least a portion of the outer surface 222 of the drum 220 and such that the longitudinal protuberances 214, 234 penetrate the grooves 224. The web material 270 is supplied to the apparatus from web material supply means 272. The web material 270 is then fed through the nip between the first roll can and the outer surface 222 of the drum 220. Subsequently, the web material is fed through the nip between second rolls 230 and the outer surface 222. The apparatus can further comprise a final roll 250, also having an outer surface 252 forming a nip with drum 220.

The grooves of the drum 220 can have any suitable shape to create the desired shape of corrugations. For example, the grooves of the rolls can be in the form of rectangles, triangles, sinusoidal curves, circular segments hyperbolic, parabolic, triangular square, and the like. For ease of manufacturing, sharp corners and edges are preferably rounded to a radius. The intermeshing protuberances are preferably of the same general shape as the grooves, although individual dimensions can be smaller so as to allow a predetermined spacing for the web to fit in without undue friction. If the grooves and protuberances fit too tightly, operation will become more difficult, or the web may be unduly compressed or even damaged.

The "pitch" (i.e. number of grooves per unit length perpendicular to the extension of grooves) is defined by the intended use and also depends on the thickness of the primary web material. The distance between two adjacent grooves can be less than 15 times the caliper of the primary web (as determined according to the test described hereinafter), preferably less than 8 times, and more preferably less than 5 times the caliper, but also can be more than 1 time, but is preferably more than 2 times, and more preferably more than 3 times the caliper.

Also the depth of the grooves depends upon on the desired shape of the corrugated web as well as on the thickness of the primary web. Thus, a groove can have a depth which is less than 15 times the caliper of the web, preferably less than 8 time, and more preferably less than about 5 times the caliper, but can also be more than 1 time, preferably more than 2 times, and more preferably more than 3 times the caliper.

Figure 3:
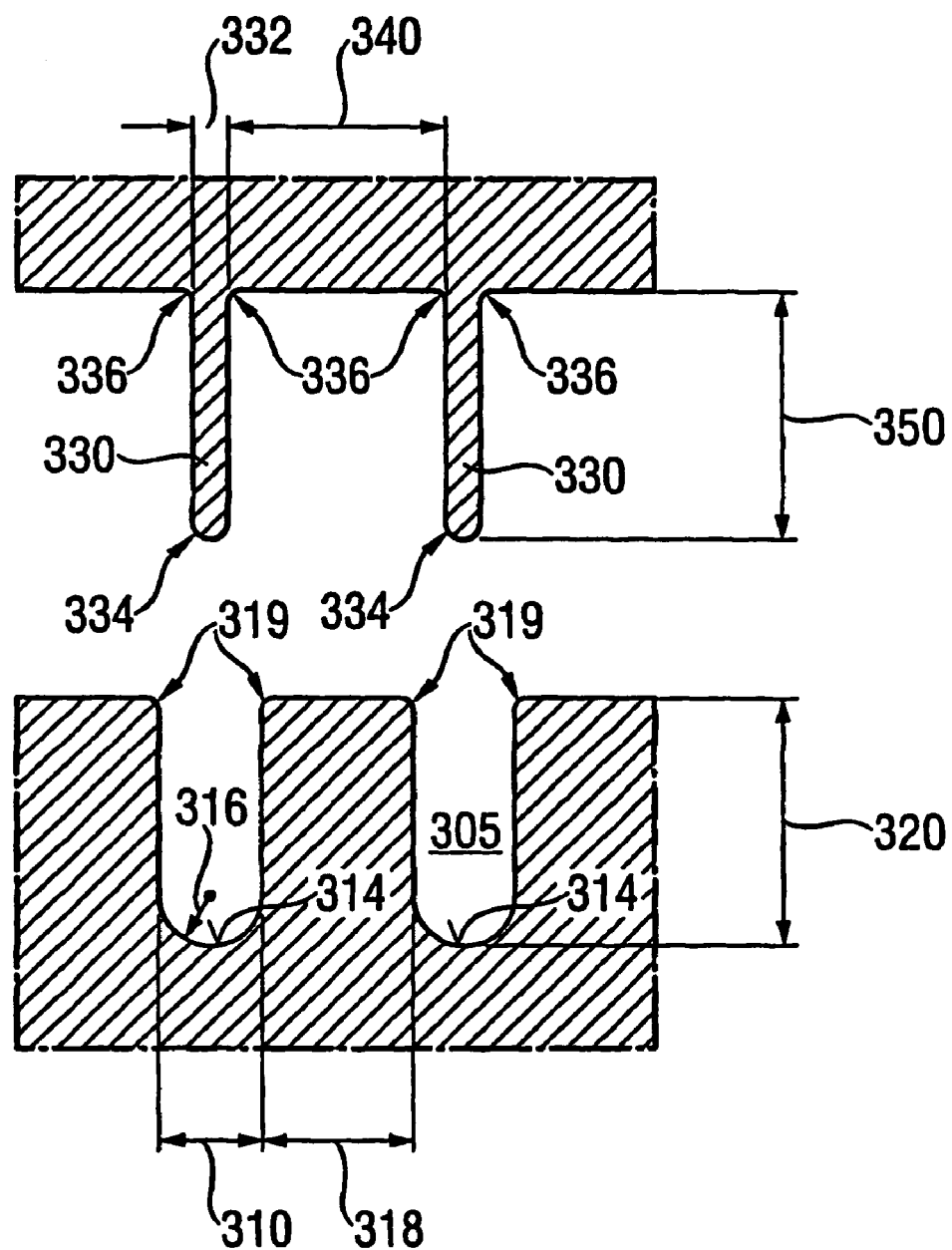
FIG. 3 shows a cross-sectional view of an exemplary groove—protuberance arrangement.

Neither pitch, nor depth nor shape of the grooves, and protuberances where appropriate, need to be the same and constant over the width of the drum. For example, when creating longitudinal corrugations as with the apparatus described in the above, the corrugations in the center of the web can be deeper, or more spaced apart from neighboring corrugations than closer to the edges of the web. An exemplary cross-sectional view of a groove/protuberance arrangement is depicted in FIG. 3, exemplifying a useful design for corrugating a thermoplastic fibrous web having a caliper of about 0.7 mm with the following dimensions: The grooves (305) have an essentially rectangular trough having a width (310) of 1.2 mm, separated from next groove by a ridge having a width (318) of 1.8 mm. The bottom of the trough (314) is rounded by a radius (316) of 0.6 mm, and the edges of the ridges by a radius (318) of 0.15 mm. The groove has a depth (320) of 3 mm. The intermeshing protuberances (330) have a width (332) of 0.4 mm, rounded to a radius (334) of 0.2 mm, and the corners can have a radius (336) of 0.15 mm. The distance (340) between two adjacent protuberances is 2.6 mm, and the protuberances have a height (350) of 3 mm.

Figure 2C:
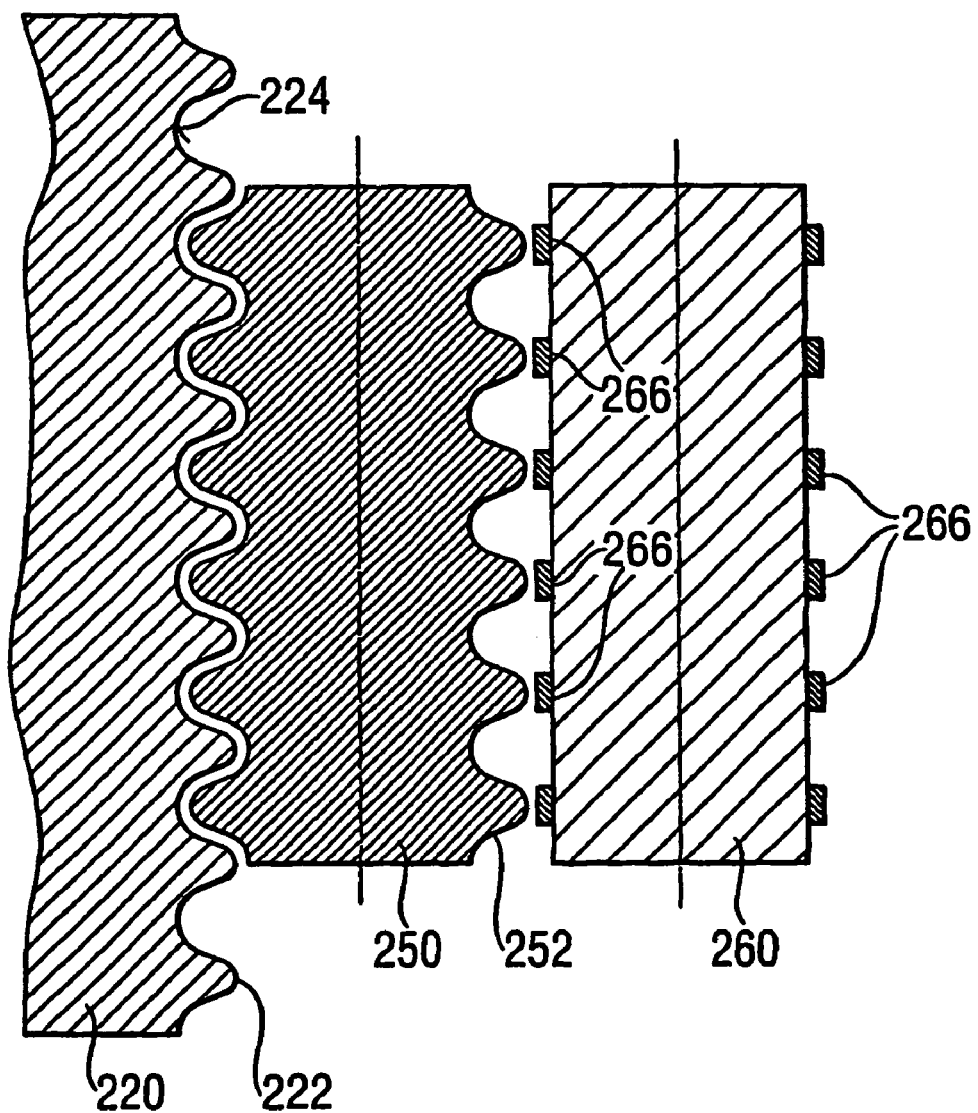
FIG. 2C shows a detail of the apparatus.

The final roll (250) transfers the corrugated web to the embossing roll (260). As schematically shown in FIG. 2C, this final roll can be corrugated—in analogy to the second rolls—also intermeshing with the grooves of drum 220. Optionally, the grooves of the final roll 250 can be removed in regions corresponding to the bonding pattern of the embossing roll 260. Alternatively, the final roll 250 can be a smooth roll.

A process of forming the corrugations is also schematically represented in FIG. 2A, showing a web (270) being is unwound from a supply roll (272) to the first roll (220) of the apparatus (240). As depicted in a schematic perspective partial view of the drum (220) in FIG. 2B, the drum, intermeshes with the first of the second rolls (210) such that the web is deformed into a first corrugation. When intermeshing with further second rolls, further corrugations are formed, and the width is reduced even further. As the web is held essentially unrestricted at its longitudinal side margins (280), these will move inwardly. In other words, the overall projected width (the straight distance between the longitudinal side margins) will be reduced from the width at the point where the material is fed into the apparatus (282) to the width of a partially or completely corrugated material (284).

Respective rolls are pressed together by means well known in the art, but excessive pressure should be avoided. Typical pressures range from about 2 to about 10 bar.

Alternatively, instead of the grooved rolls, a flat guide bed can be used having flat grooves with increasing groove depth. See for example the above referenced WO 96/00625 (Raidel). Also, a corrugation forming means as described in EP-A-0.341.993 can be used.

Once the corrugation have been formed, it is desirable to maintain their shape for further process steps and/or during their intended use. Conventional processes such as referred to in the above, achieve this by adding a further material, such as by applying an adhesive or by stabilization by means of a second, flat web material to which the corrugated web is attached. For example, the corrugated material can be attached to the second web such as by adhesive gluing in the "valley regions" of the corrugation (see above referenced U.S. Pat. No. 5,906,879), or by melt-fusion in the valley region, such as described in the above referenced EP-application 99124637.

In contrast to these approaches, the present invention aims at providing a corrugated web material comprising fibrous materials exhibiting these benefits of bonding without an added material but rather by creating a "self-bonded" web.

The term "self-bonding" or "autogenously bonding" refers to a web, and in particular to a fibrous web, having a sufficient amount of thermally compatible fibrous material or materials in the web, which upon melting through the impact of energy such as heat, and/or pressure, or ultrasonic energy, can bind together. "Thermally compatible" refers to the fact, that—if it is one type of material—it can be melt or heat-bonded to itself, or—if it refers to different materials—these materials have melting points and properties allowing them to melt- or heat-bond to each other. Formed and heat-bonded webs do have a sufficient inherent structural strength and coherence without any adhesive materials added to the structure. Useful materials allowing heat-or melt-bonding have been described in the above in the context of forming the heat bondable primary webs.

A preferred approach to this self-bonding is by embossing part of the structure, such as by well known hot embossing, or ultrasonic bonding or combinations thereof. This energy input increases the temperature of at least parts of the web such that parts of the fibers can bond to each other upon cooling.

In contrast to the bonding with a line pattern parallel to the corrugations lines as disclosed e.g. in WO96/00625 (refer to the FIG. 11. therein), the present inventions applies a bonding pattern connecting at least two neighboring corrugation lines.

Figure 2E:
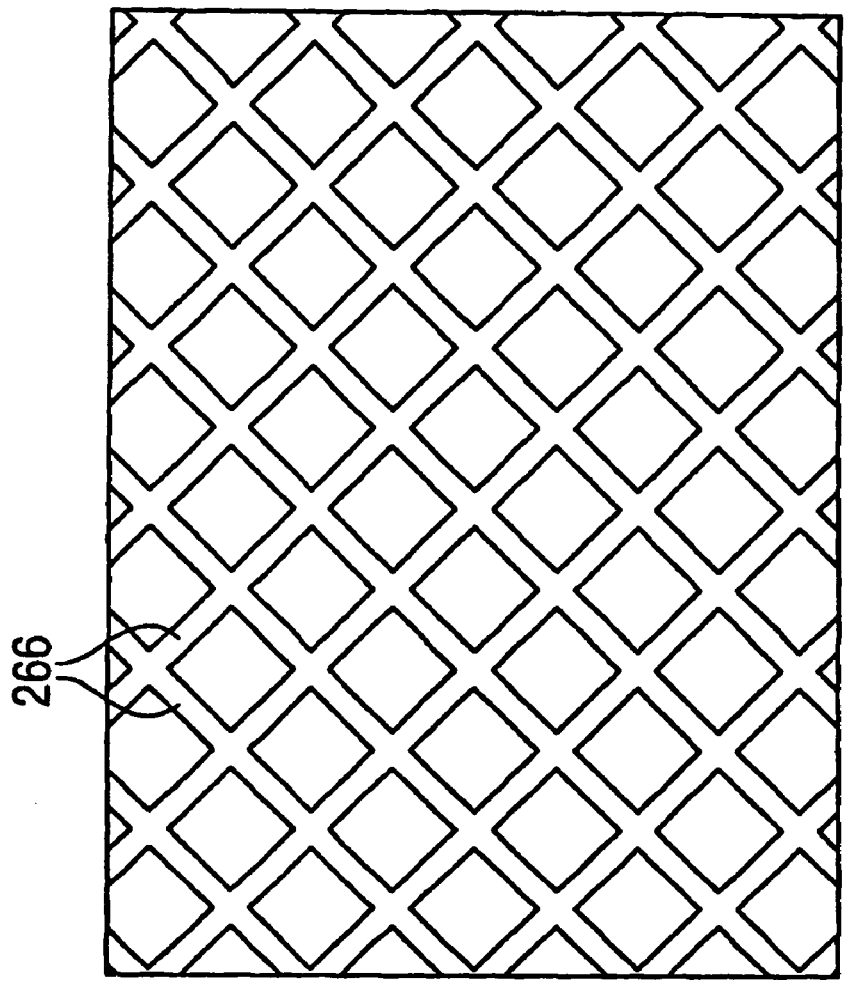
FIG. 2E shows the planar projection of the surface of the embossing roll.
Figure 2D:
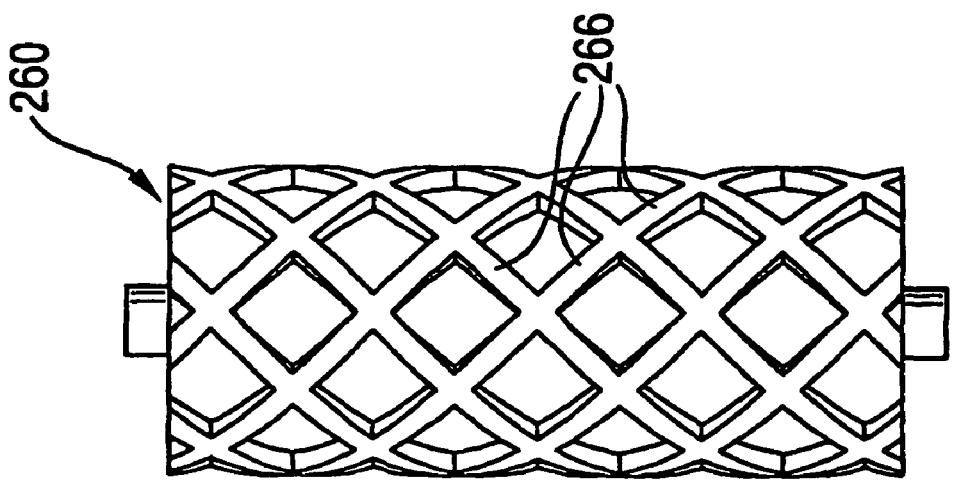
FIG. 2D shows an embossing roll of this apparatus.

As depicted in FIGS. 2A, C, D, and E, one approach is to use a patterned embossing roll (260) for this embossing, which can be performed while the corrugated web is still in grooved structure, such as a guide bed, or a shaped roll, such as the final roll 250 as shown in FIG. 2D, where respective grooves are filled by the web. FIG. 2D shows a top view of an embossing roll, and FIG. 2E a flat projection of the embossing surface of the embossing drum.

Figure 4A:
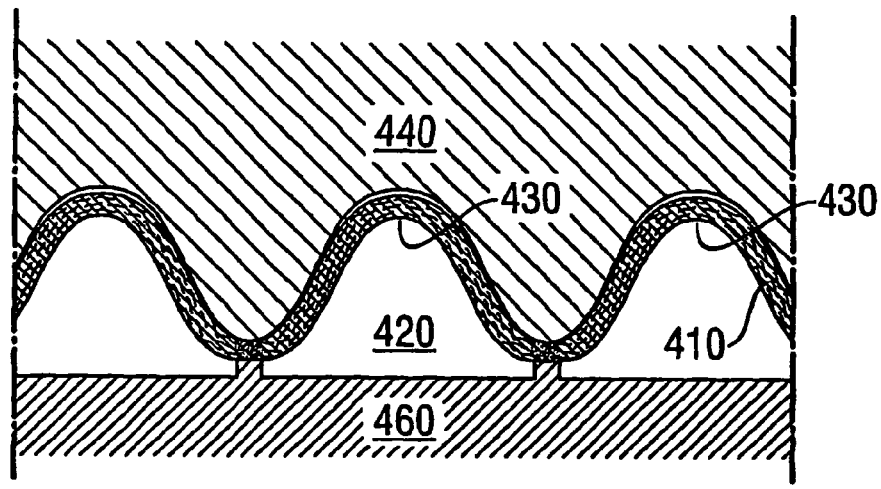
FIGS. 4A, B and C show exemplary cross-sectional views through an embossed web as positioned between a roll and the embossing roll.

As further detailed in FIG. 4A, the embossing will essentially take place in the "valleys" (420) of the web (410), now defined as the parts radially outwardly of the shaped or grooved roll (440) or from a grooved guide bed respectively. This is considered to be a "valley" region, as this part of the corrugated web will be somewhat flattened by the embossing roll (460) compared to the opposite side of the web, where the "peak" regions (430) remain more lofty than the embossed "valley" regions.

Thus, the "valley" regions are more suitable to form a "basis" especially when these structures are integrated into an absorbent article, which will preferably be done in a way such that the surface of the corrugated web with the "peaks" is oriented towards the wearer during the intended use, and the "valley" side is oriented away from the wearer or towards the garment side of the article.

Figure 4B:
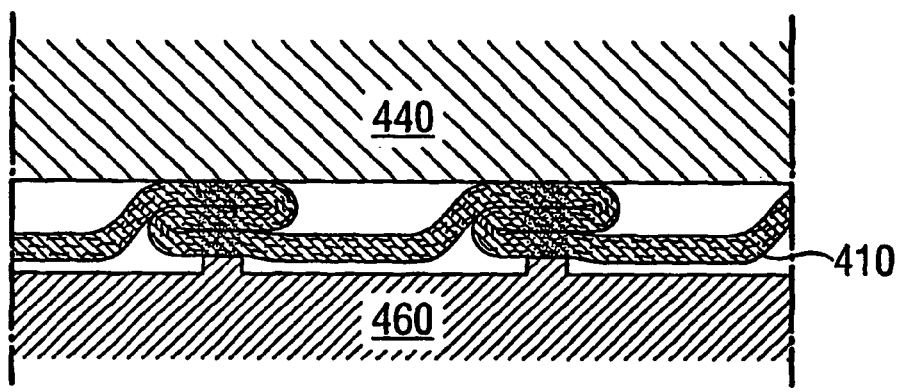
Figure 4C:
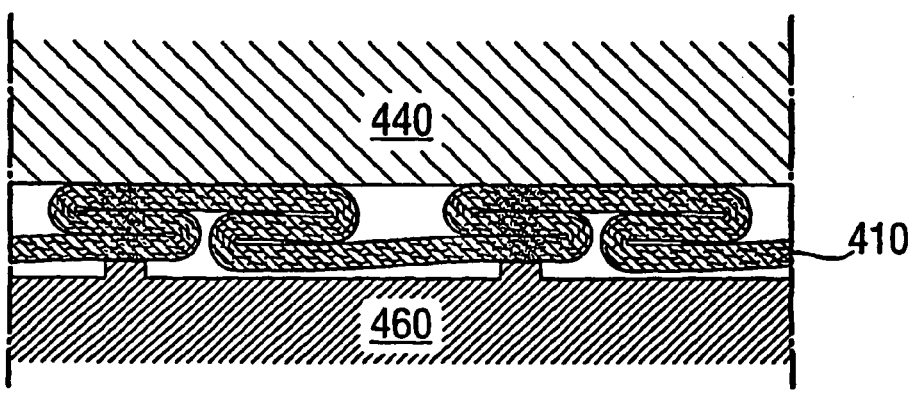

Alternatively, the final roll can be a smooth roll without grooves at the surface. Then, upon running over this roll, the corrugations will deform and flatten, such as schematically depicted in FIGS. 4B and 4C feeding this structure through the embossing nip between final roll 440 and patterned embossing roll 460, will result in bonding overlapping and overlaying sections together. Releasing the web from the embossing roll will allow the unbonded regions to recover their corrugation shape resiliently, while the overall corrugation pattern is stabilized by the bonded regions of the primary bonding pattern.

As a further option, the final roll 250 (FIG. 2) can be shaped to have grooves except for regions matching the embossing pattern of the embossing roll 260, e.g. by removing the ridges between adjacent grooves in these regions.

Figure 5A:
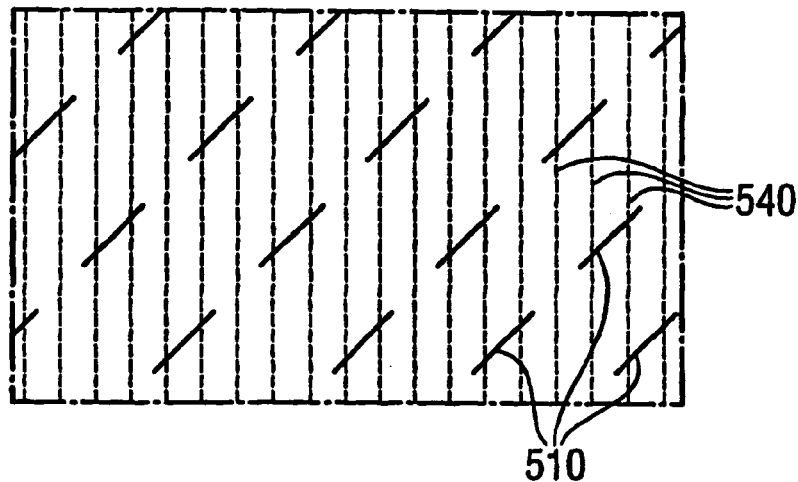
FIG. 5A to F show examples of primary bonding patterns.
Figure 5B:
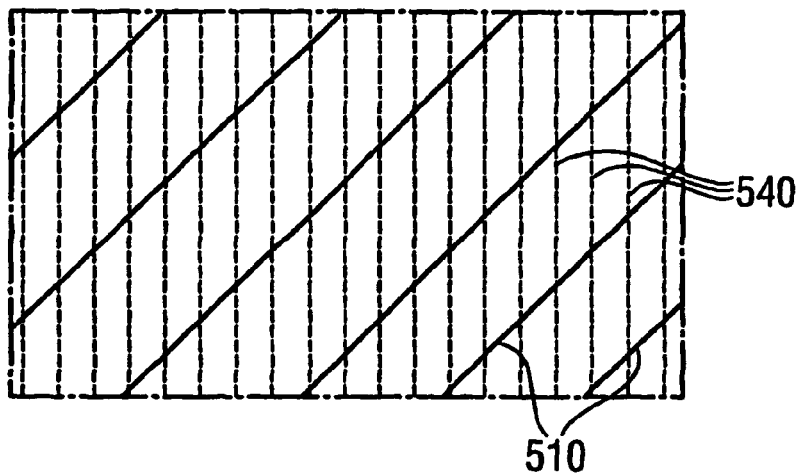
Figure 5C:
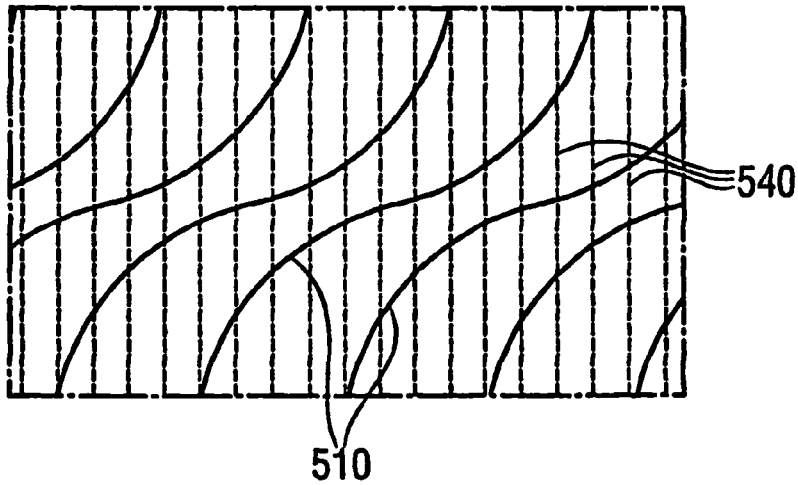
Figure 5D:
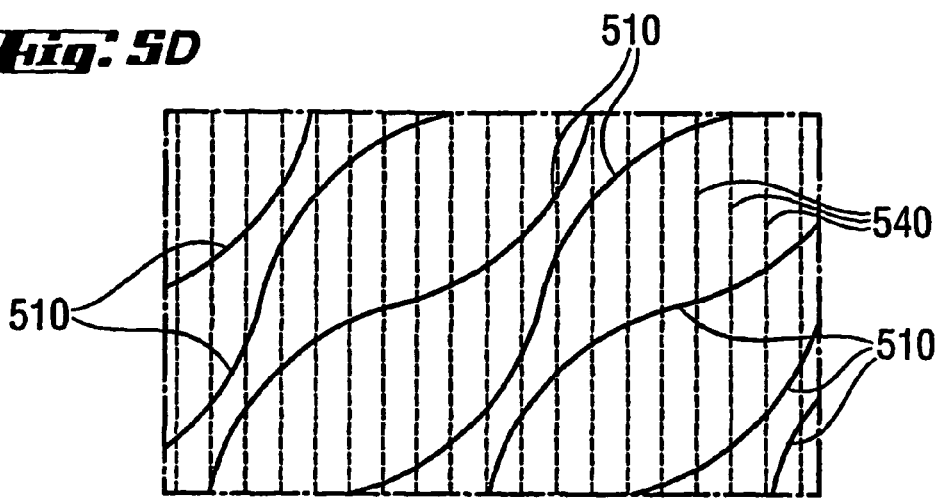

FIGS. 5A to F depict schematically various examples of primary bonding patterns, all relative to the orientation of the corrugations as indicated by the (dashed) corrugation pattern lines 540. FIG. 5A shows a plurality of primary pattern lines 510 all oriented in parallel and intersecting the corrugation lines, each line connecting two neighboring corrugation lines. Provided that there is a sufficient length of the material, each corrugation line is connected to each of its neighboring corrugation lines by at least one of the primary pattern lines. In FIG. 5B, the primary pattern lines 510 are continuous straight lines. The primary patterns lines do not need to be straight lines, but can be curvilinear, such as sinusoidal or any other regularly repeating form, such as depicted in FIG. 5C with sinusiodal lines 510, essentially parallel to each other, and offset perpendicularly to the general direction of the curvelinear lines. In FIG. 5D, this pattern in modified in that the parallel lines 510 as in FIG. 5C are also offset to each other along the general direction of these lines.

Figure 5E:
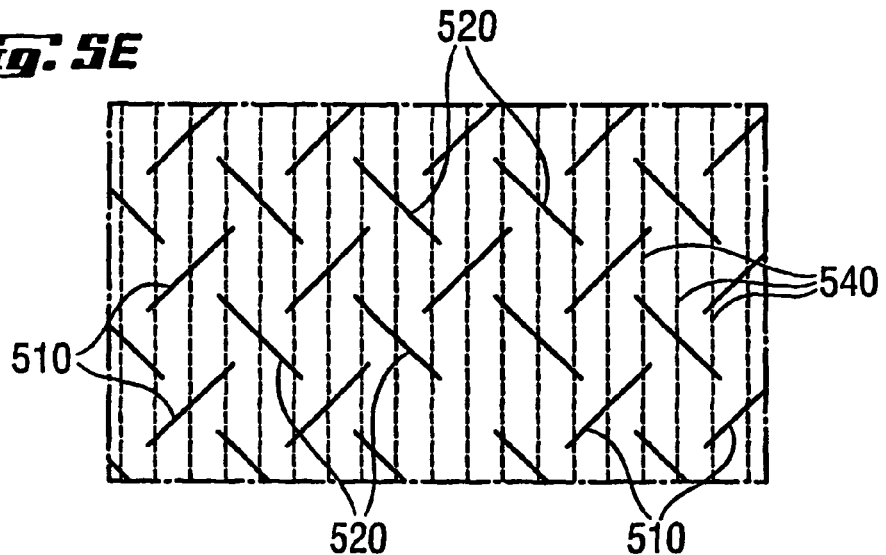
Figure 5F:
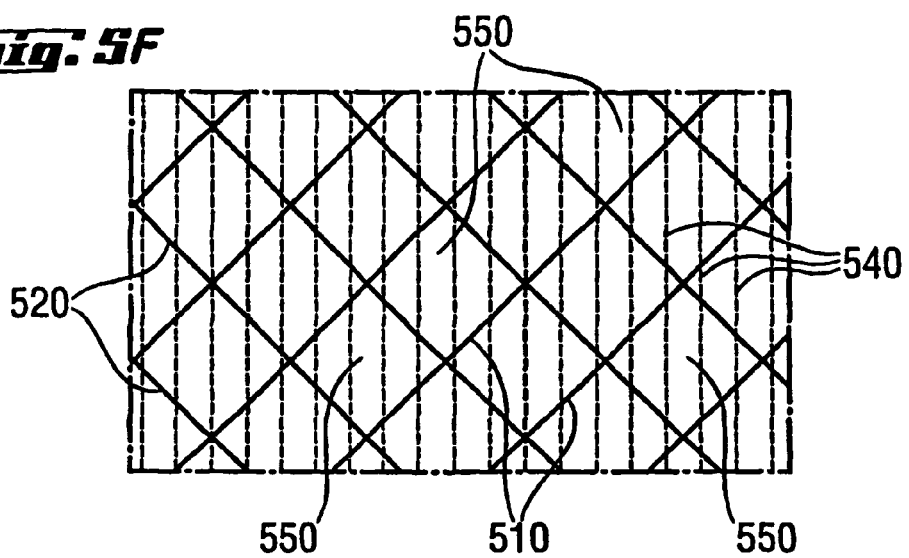

FIG. 5E depicts a primary bonding pattern having a plurality of first and second primary bonding pattern lines (510 and 520 respectively), oriented perpendicularly to each other, and non-parallel to the direction of the currugation lines 540. Each of the first and the second primary bonding pattern lines connects in this case three corrugation pattern lines. FIG. 5F depicts a further primary bonding pattern formed of intersecting continuous first and second primary bonding pattern lines 510 and 520, thereby forming regions or arrays 550 of corrugations not bonded by the primary bonding pattern. In this example, these regions or arrays contain four or five corrugation lines. It has been found that these regions or arrays (550) are preferably sized such that they contain at least 3, preferably 5, or even more preferably at least 9 corrugation lines (540), but preferably not more than 20, preferably less than 15 and even more preferably less than 12 corrugation lines are intersected.

Also, the first and the second linear pattern do not need to be straight lines, but can be curvelinear as discussed, and the first and second primary bonding pattern lines do not need to symmetric to each other, but can, for example, be sinusoidal curves of different amplitude and/or wavelength.

Figure 6:
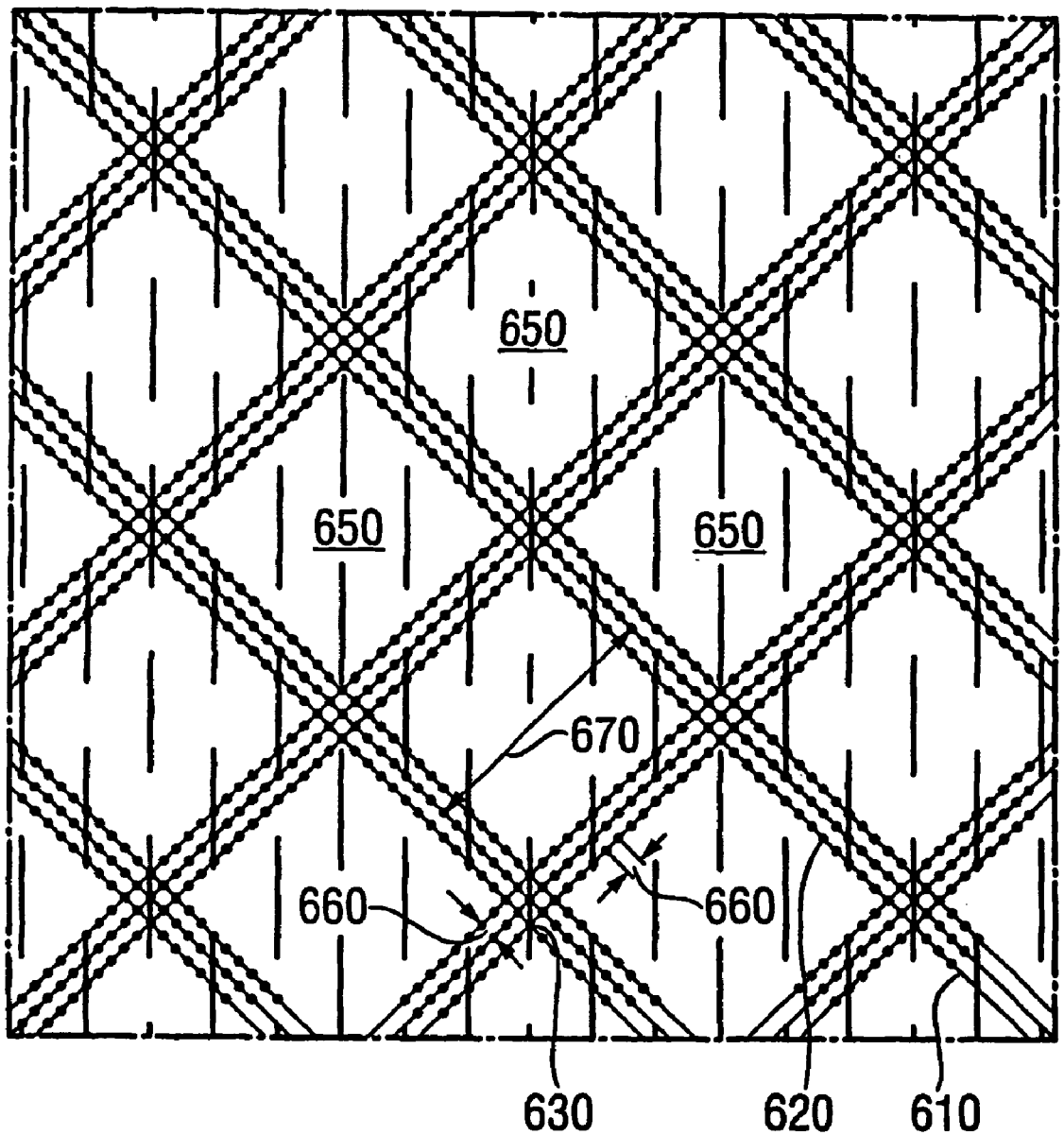
FIG. 6 shows an exemplary primary bonding pattern formed of a secondary bonding pattern.

The primary bonding pattern lines can be, but do not need to be solid lines, such as solid embossing lines as depicted in FIG. 5, but—as exemplified in FIG. 6—can consist of a secondary bonding pattern (620), such as a plurality of dots or points (630) of a certain size arranged such that the distance (660) between adjacent dots within this secondary pattern is significantly different than the center-to-center distance (670) between two adjacent, non-intersecting primary pattern lines (610) forming the essentially enclosed arrays (650).

Improved properties of corrugated web materials according to the present invention are primarily in the area of effective and efficient use of resources, such as by providing a good resiliency without unnecessary material usage. Resiliency of a web as such can be measured by determining the caliper before and after submitting the web to certain loads for a certain period of time. However, in order to compare efficient use of materials, it has been found useful to establish the loft of the material which—being expressed in units of μm/g—provides a measure for an efficient spacing capability, and which can be determined by normalizing the caliper after aging by the basis weight of the material.

Hence, a suitable material exhibits a low pressure aging loft (as described hereinafter) of at least 18 $[\mu m/(g/m^2)]$ preferably of more than 21 $[\mu m/(g/m^2)]$ and even more preferably of more than about 23 $[\mu m/(g/m^2)]$. A suitable material exhibits a high pressure aging loft (as described hereinafter) of at least 11 $[\mu m/(g/m^2)]$, preferably more than about 13 $[\mu m/(g/m^2)]$, and even more preferably of more than about 18 $[\mu m/(g/m^2)]$.

Suitable articles according to the present invention comprise the corrugated webs—or cut out sections thereof—as described in the above. This is particularly beneficial for articles, which are produced in large quantities at high speeds, such as disposable absorbent articles. It is even more beneficial for such articles, which require for performance reasons—such as to enhance fluid handling performance—an open structure having a low density during use, but which have a small volume or high density during transport for effective transport between the manufacturing and the end user. Under such conditions, resiliency is an important property so as to allow the compression of such structures for small volume packaging, but to also allow "spring back" upon removal from the package before its intended use.

Further, for such articles, efficient material usage is an important feature, i.e. it is undesirable to have any components which do not directly improve the performance of the articles. Henceforth, it is desired to get a maximum loft of the material to achieve best performance with least material usage.

In this area, articles comprising a self-bonded corrugated web according to the present invention are superior to articles comprising, for example, a corrugated web further comprising a binder material, such as an adhesive, or a support structure such as a support web.

Self-bonded corrugated webs according to the present invention can suitably be used as a material generally referred to as "acquisition material", in the context of receiving bodily exudates, such as urine, menses or fecal material. As such, the corrugated webs are arranged in the article so as to readily receive these exudates, and thus can be part of the article surface which is oriented towards the wearer, or can underlay a top layer adapted to readily allow the passage of such exudates to the corrugated self-bonded web.

In a particular embodiment, the web is oriented so as to have the embossed "valleys" away from the wearer, and the more open "peaks" towards the wearer.

The absorbent article further comprises absorbent cores, optionally including further layers or zones adapted for liquid handling as acquisition, distribution, or storage of liquids, and at least a backsheet, optionally further various chassis elements so as to prevent soiling of the exudates and to maintain the article on the wearer, or a topsheet. Various of such articles are well known in the art, and—as long as the positioning requirements are met—are compatible with the self-bonded corrugated webs of the present invention.

EXAMPLES

An exemplary embodiment of the self-bonded web of the present invention is a modified 43 $g/m^2$ resin bonded PET web, such as commercially available under the designation 6850ABPET from PGI Nonwovens, Neunkirchen, Germany, having a flat caliper of about 0.7 mm under a pressure of 0.5 kPa. This web has been shaped into linear MD oriented corrugations, as described in more detail above. The primary web had a width of 125 mm, which has been reduced by corrugation to a width of 90 mm, thus, having a corrugation factor of about 1.4 and a basis weight of about 60 $g/m^2$.

This corrugated material has been thermally bonded by applying sufficient pressure with a primary embossing pattern of parallel first and second straight lines, intersecting each other at an angle of 90° and the orientation of the corrugations at and angle of 45°. Each of the first and second lines are spaced apart 25.4 mm. Thus, a square pattern is formed, with approximately 10 corrugations per each of the diamonds.

The primary embossing pattern was formed by a secondary embossing pattern consisting of three parallel rows of bonding points, each point being a square of about 0.5 mm spaced apart from neighboring bonding points by about 0.5 mm, arranged such that the secondary patterns of two intersecting first and second lines of the primary pattern overlap smoothly.

The embossing is arranged such that between two neighboring embossing points some compression and embossing is performed, such that each primary embossing line were about 2.5 mm wide with points of high compression corresponding to the bonding points, and areas of lesser compression between these points.

The web has been self-bonded while the corrugated material was still supported in the grooved shaping roll, so as to emboss the "valley" regions of the corrugations only, while the remaining portions the corrugations were not bonded.

The corrugated and self-bonded web exhibited improved performance characteristics, when compared to a conventional corrugated material bonded to a support structure (see comparative example).

Comparative Example 1

As a first comparison, the starting material without any corrugations has been tested as first reference.

Comparative Example 2

The same starting material as for the example has been corrugated into the same shape, but then bonded to a support layer formed from an otherwise identical material as the starting material except for having a basis weight of 20 g/m². The bonding was achieved by melt bonding lines extending along the "valley" regions of the corrugations.

Consequently, the overall resulting basis weight was about 77 g/m². All materials have been submitted to the accelerated aging compression Test, as described hereinafter, and tested for their loft, i.e. their caliper normalized for the basis weight.

TABLE 1

Test results

|  | basis weight [g/m²] | loft high pressure [μm/(g/m²)] | loft low pressure [μm/(g/m²)] |
| --- | --- | --- | --- |
| Example | 55 | 11.5/12.9 | 18.9/18.9 |
| Comp. Ex. 1 | 43 | 7.0 | 10.5 |
| Comp. Ex. 2 | 77 | 11.9 | 17.1 |

Henceforth, as shown by the data in Table 1, a material according to the present invention not only provides a more simplified approach to compression resistant material, but also a better degree of compression resistance than comparable conventional materials.

Test Methods

The testing for caliper and loft is performed on a part of the sample which is a representative area of the primary pattern as well as of the unbonded corrugated regions. Preferably, the center of the sample is considered to be an intersection of the first and second lines of the primary pattern. If necessary, the size of the pressure foot needs to be adjusted so as to cover such a region, and so needs the added weight to be adjusted to maintain the pressures as indicated in the test description.

Basis Weight

A sample of the material is selected, so as to be representative for the area for which the caliper has been determined. This sample is cut out by suitable methods, such as by a circular cutter, or a pair of scissors, corresponding to an readily determinable area. This cut out sample is weighed on a suitable scale having a precision of higher than 1% of the sample weight. The basis weight is then determined by dividing the weight by the area, generally expressed in [g/m²].

Low Pressure and High Pressure Caliper

The caliper of a material is determined by a suitable caliper gauge, such as Type EG-225 available from ONO SOKKI Technology Inc. Ill. US, with an appropriate gauge stand, having an aluminum circular sample foot of 41 mm diameter, having a weight of foot of 80 g. The caliper is generally expressed in [μm].

The caliper measurement is executed under either of two pressure conditions, a "low pressure caliper" and a "high pressure caliper".

Low pressure caliper corresponds to an exerted pressure of 750 Pa, or—for the above mentioned sample foot—of 16 g additional weight. High pressure caliper corresponds to an exerted pressure of 12733 Pa, or—for the above mentioned sample foot—of 1560 g additional weight.

Accelerated Aging Compression Test

A single layer of a test sample is submitted for 48 hours under 37° C. to a pressure of 3470 Pa, which corresponds for a sample having an area of 28.27 cm² to a weight of 1000 g. The caliper is determined after 120 sec. after removal of the aging weight.

Loft

The loft of a material is determined by dividing the caliper by the basis weight, and is generally expressed in [μm/(g/m²)].

Following the high pressure or low pressure distinction for caliper, corresponding low pressure or high pressure loft results.

The invention claimed is:

1. A self-bonded corrugated web comprising a primary pre-bonded web layer of thermoplastic fibers having a substantially uniform thickness in a z direction and having a CD orientation and a MD orientation, the primary pre-bonded web arranged to form corrugations oriented in a corrugation pattern of parallel corrugation lines wherein said corrugations lines are essentially parallel to the MD orientation of said web layer, the corrugated web includes a primary bonding pattern of heat- or melt-fusion bonded regions forming a plurality of first primary bonding pattern continuous lines and second primary bonding pattern continuous lines, the first primary bonding pattern continuous lines are parallel to each other and the second primary bonding pattern continuous lines are parallel to each other, the first primary bonding pattern continuous lines are non-parallel to the second primary bonding pattern continuous lines, the first primary bonding pattern continuous lines and the second primary bonding pattern continuous lines are arranged non-parallel to the corrugation lines, the first and second primary bonding pattern continuous lines intersect at least two of the corrugation lines for stabilizing the corrugations of the corrugated web and wherein the continuous lines of said first primary bonding pattern intersect the continuous lines of said second primary bonding pattern, wherein said first and second primary bonding pattern continuous lines form regions of corrugations that are unbonded by said primary bonding pattern.

2. A self bonded corrugated web according to claim 1, wherein each of the corrugation lines of the corrugation pattern is connected to at least one neighboring corrugation line by at least one primary bonding pattern line.

3. A self bonded corrugated web according to claim 1, wherein the regions unbonded by the primary pattern contain at least 3 corrugations.

4. A corrugated web according to claim 1, wherein regions unbonded by the primary pattern contain less than 20 corrugations.

5. A self bonded corrugated web according to claim 1, wherein the primary bonding pattern lines are continuous straight lines.

6. A self bonded corrugated web according to claim 1, wherein the primary bonding pattern further comprises a secondary bonding pattern comprising a plurality of bonding points.

7. A self bonded corrugated web according to claim 1, wherein the web exhibits a low pressure loft of at least 18 [μm/(g/m²)].

8. A self bonded corrugated web according to claim 1, wherein the corrugated web exhibits a high pressure loft of at least 11 [μm/(g/m²)].

9. A self bonded corrugated web according to claim 1, wherein the bonding is patterned embossing.

10. A self bonded corrugated web according to claim 1, wherein the corrugations are deformed in the region of the primary bonding pattern so as to form overlaying layers of the primary web which are bonded to each other.

11. A self-bonded corrugated web having a primary pre-bonded web layer of thermoplastic fibers having a substantially uniform thickness in a z direction and having a CD orientation and a MD orientation, the primary pre-bonded web arranged to form corrugations oriented in a corrugation pattern of parallel corrugation lines wherein said corrugations lines are essentially parallel to the MD orientation of said web layer, the corrugated web comprising:

a primary bonding pattern of heat- or melt-fusion bonded regions forming a plurality of first primary bonding pattern lines and second primary bonding pattern lines, wherein said first primary bonding pattern lines are parallel to each other and said second primary bonding pattern lines are parallel to each other, wherein said first primary bonding pattern lines are non-parallel to said second primary bonding pattern lines, wherein said first primary bonding pattern lines and said second primary bonding pattern lines are arranged non-parallel to said corrugation lines, and wherein said first and second primary bonding pattern lines are solid continuous lines that intersect at least 3 corrugations and wherein the continuous lines of said first primary bonding pattern intersect the continuous lines of said second primary bonding pattern, wherein said first and second primary bonding pattern continuous lines form regions of corrugations that are not bonded by said primary bonding pattern, wherein said regions contain at least three corrugation lines.

12. A self bonded corrugated web according to claim 11, wherein said thermoplastic fibers have a length from about 0.3 to about 7.5 cm.

* * * * *

UNITED STATES PATENT AND TRADEMARK OFFICE
CERTIFICATE OF CORRECTION

PATENT NO. : 7,427,434 B2 Page 1 of 1
APPLICATION NO. : 10/689342
DATED : September 23, 2008
INVENTOR(S) : Busam et al.

It is certified that error appears in the above-identified patent and that said Letters Patent is hereby corrected as shown below:

Column 6
Line 23, delete "." and insert -- , --.

Signed and Sealed this

Nineteenth Day of May, 2009

JOHN DOLL
*Acting Director of the United States Patent and Trademark Office*